June 12, 1973 W. H. JESSEL, JR., ET AL Plant Pat. 3,357
CHRYSANTHEMUM PLANT
Filed Sept. 14, 1971 2 Sheets-Sheet 1
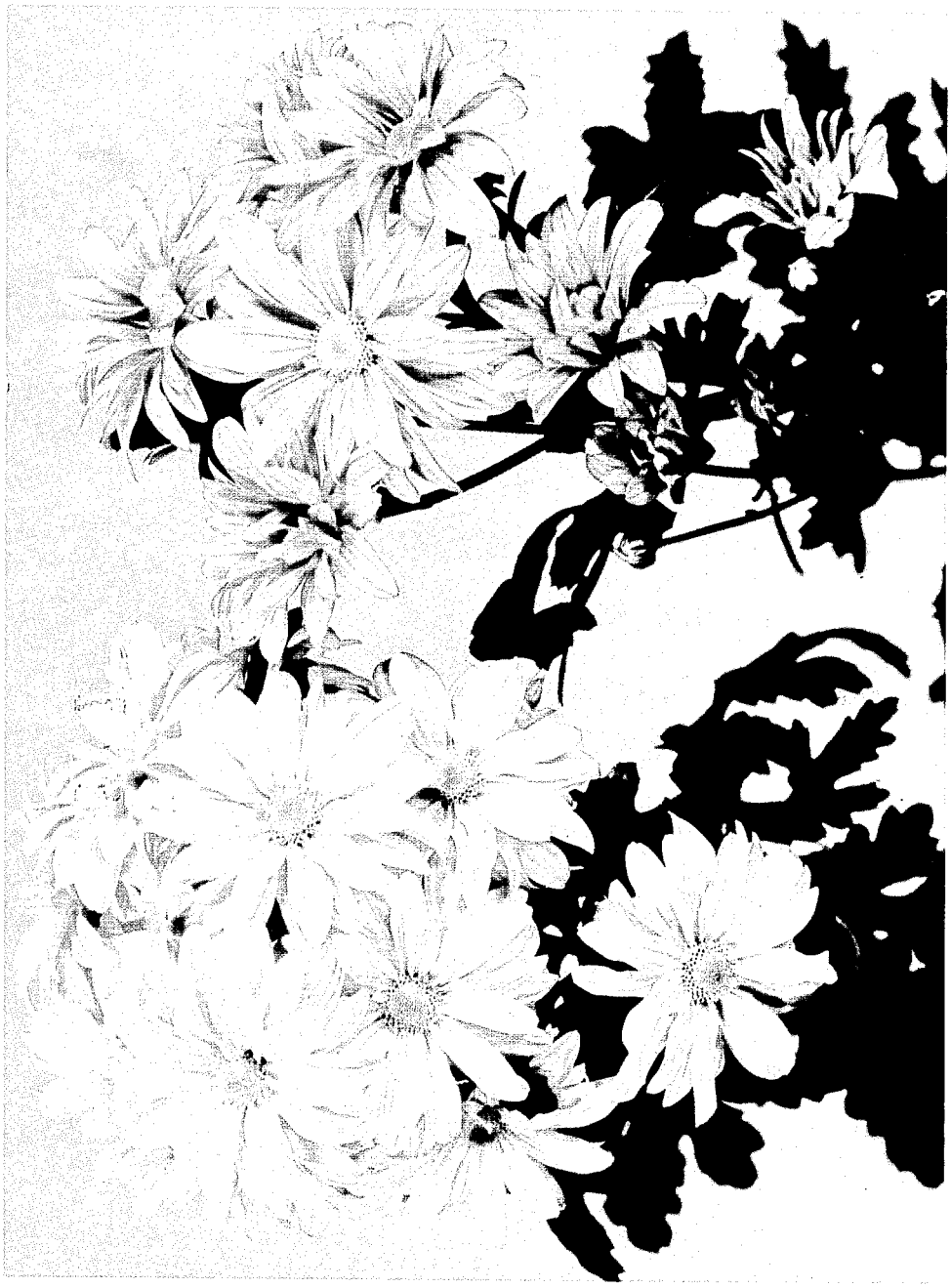

CHRYSANTHEMUM PLANT
Filed Sept. 14, 1971 2 Sheets-Sheet 2
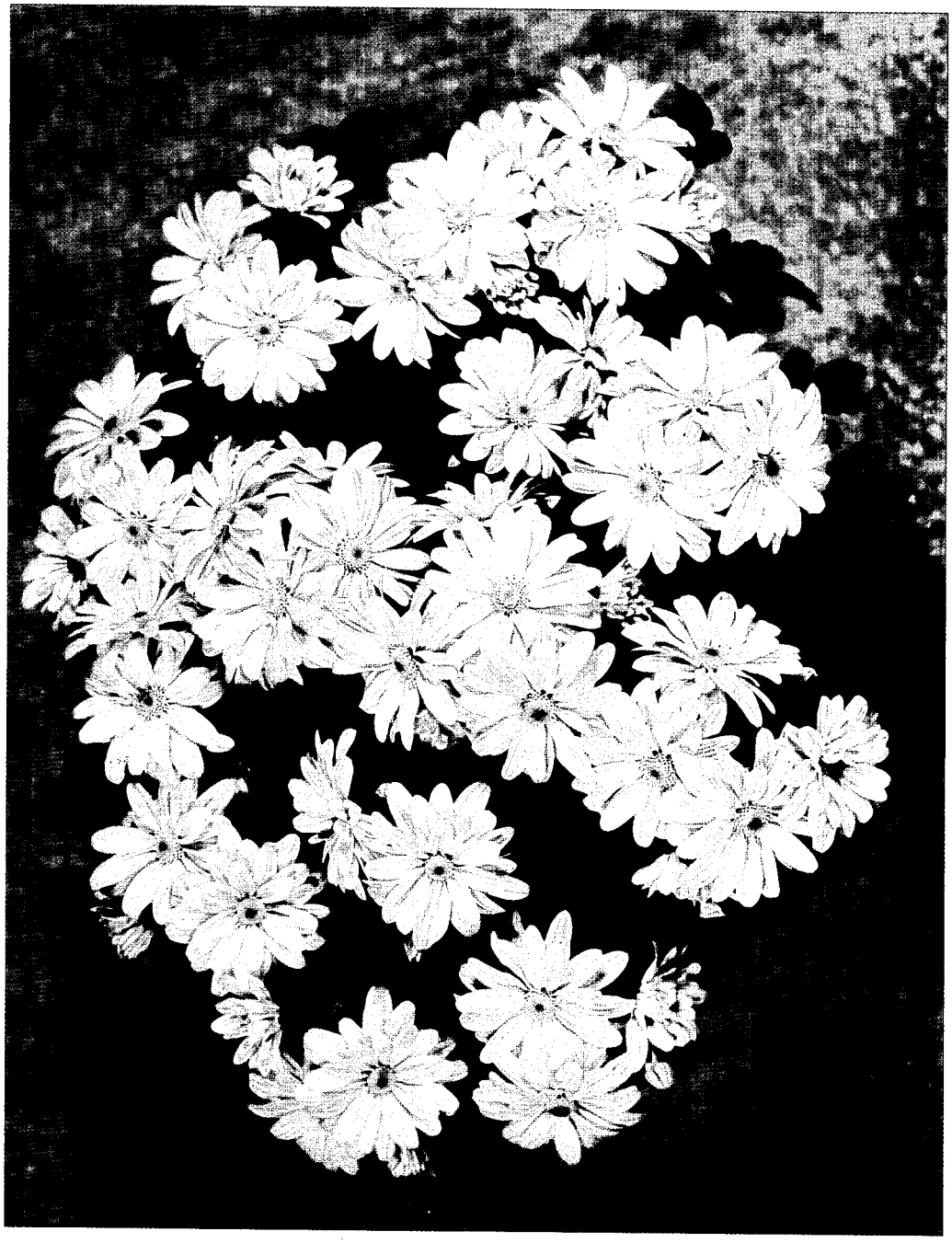

United States Patent Office

Plant Pat. 3,357

Patented June 12, 1973

3,357
CHRYSANTHEMUM PLANT

Walter H. Jessel, Jr., Doylestown, and William E. Duffett, Akron, Ohio, assignors to Yoder Brothers, Inc., Barberton, Ohio

Filed Sept. 14, 1971, Ser. No. 180,532
Int. Cl. A01h *5/00*
U.S. Cl. Plt.—74 1 Claim

The present invention comprises a new and distinct cultivar of chrysanthemum plant which is a sport of the cultivar known in the United States as Aglow, disclosed and illustrated in our pending application for U.S. Plant Patent Ser. No. 80,256, filed Oct. 12, 1970, and now P.P. 3,212.

The new cultivar is similar in certain respects to Aglow, having the same characteristics of:

(1) Flower form.
(2) Foliage size.

The new cultivar is distinguished from Aglow by the following characteristics, when grown under comparable conditions:

(1) Flowers approximately ¼″ smaller in diameter.
(2) More prolific, producing approximately 3 to 4 more flowers per stem.
(3) A more orange coloration.
(4) Approximately 2″ to 3″ less vigor.
(5) A lighter foliage color.
(6) Approximately three days earlier response.
(7) A more uniform response within a flowering block.

The new cultivar was selected from a flowering block of the parent cultivar at Barberton, Ohio, and when asexually reproduced by cuttings at Barberton, Ohio, has been found to retain its distinctive characteristics through successive propagations.

The new cultivar when grown in the vicinity of Barberton, Ohio, has a response period of approximately 9 weeks as a spray pot and has a mid 9 to early 10 week response as a cut spray, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from October through June as a pot mum; mid-September through mid-November and April through mid-June as a cut spray; in coastal California, year-round as a pot mum; October through July as a cut spray, and in southern Florida, December through April as a pot mum and cut spray.

The accompanying drawings show the unique characteristics of the new cultivar, with the color being as true as possible with color illustrations of this type. Sheet 1 is a comparison view of the new cultivar and the parent cultivar Aglow on the right. This photograph was taken of a flowering in May under higher finishing temperatures. Sheet 2 comprises a photograph of the new cultivar as a pot mum, and was taken of a flowering in early February under cooler finishing temperatures. The somewhat darker flower color due to the cooler finishing temperatures will be noted.

In the description which follows, color references are to the Munsell Color Book, 1963 edition, and comparisons are made with the parent cultivar Aglow. Where only a single value or description appears for the new cultivar, the same value or description applies as well to the parent cultivar.

Botanical classification: *Chrysanthemum morifolium*

| | Orange Aglow | Aglow |
|---|---|---|
| Bloom: | | |
| Size | 2½″ | 2¾″. |
| Fully expanded | 4″ | 4¼″. |
| Borne | Clustered on elongated pedicel | |
| Stems | 6″–10″ | Elongated pedicels 8″ to 12″ long. |
| Form | Daisy (single) | |
| Permanence | 7–10 days | |
| Color: | | |
| Center of flower | Yellow green, 5GY5/6 to 6.25Y7/12 | Yellow green, 5GY5/6 to 6.25Y7/12. |
| Base of petals | Orange bronze, 2.5GY7/8 | Approximately bronze, 10R4/10 to bronze, 5YR6/12. |
| Inside of petals | Bronze, 6.25YR6/12 to orange bronze, 8.75YR7/14 | Approximately bronze, 8.75YR7/14 to light bronze, 10YR7/12. |
| Reverse of petals | Light bronze, 10YR7/10 to yellow bronze, 5Y8.5/10 | Yellow green, 5Y8/8. |
| Tonality from a distance | Orange | Red bronze. |
| Discoloration | Light bronze, 8.75YR7/14 | Light bronze, 10YR7/12. |
| Petals: | | |
| Texture | Smooth | Rough. |
| Appearance and form | Open at base, broaden quickly, two main keels at bottom, tapering to a blunt point. | Deeply keeled with ridges, tapering to a blunt point. |
| Arrangement | Composite, whorled on a single receptacle | |
| Persistence | Resists shatter | |
| Fragrance | Typical chrysanthemum | |
| Reproductive organs: | | |
| Stamen, anthers | 200+ | |
| Pollen | Abundant to none (functional sterility) | |
| Arrangement | Clustered in center of flower, if present | |
| Styles | Present in both ray and disc florets | |
| Length | Short | |
| Ovaries | At the base of petal attached to receptacle | |
| Plant: | | |
| Form | Herbaceous | |
| Growth | Semi-upright | |
| Height | 31″–35″ as a daisy pompon when given 4–5 long day weeks and a total crop time of 13–14 weeks; 10″–16″ as a pot mum given 9 week tall treatment as outlined in the timetables of Yoder Bros., Inc., Barberton, Ohio, for the various seasons of the year. | 34″–38″ as a daisy pompon when given 4–5 long day weeks and a total crop time of 13–14 weeks; 12″–18″ as a pot mum given 9 week tall treatment as outlined in timetables of Yoder Bros., Inc., Barberton, Ohio, for the various seasons of the year. |
| Spread | 6″–8″ as a pinched pot plant | |
| Foliage: | | |
| Top side | Dark green, 7.5GY3/4 | Dark green, 10GY2/4. |
| Size | 4¼″ long, 2¾″ wide | |
| Quantity | Numerous | |
| Shape | Spatulate lobed | Palmate lobed. |
| Texture | Smooth | Smooth. |
| Ribs and veins | Prominent | |
| Edge | Deeply indented | |
| Serration | Slight | |
| Under side | Light green, 5GY4/4 | Light green, 7.5GY4/4. |
| Stipules | Base of petiole prominent | |

We claim:

1. A new and distinct cultivar of chrysanthemum characterized particularly as to its uniqueness when compared to the parent cultivar Aglow by its flowers which are approximately ¼″ smaller in diameter; its higher production, producing approximately 3 to 4 more flowers per stem; more orange coloration; approximately 2″ to 3″ less vigor; lighter foliage color; approximately three days earlier response, and its more uniform response within a flowering block.

No references cited.

ROBERT E. BAGWILL, Primary Examiner